US011925754B2

(12) United States Patent  
Ji

(10) Patent No.: US 11,925,754 B2  
(45) Date of Patent: Mar. 12, 2024

(54) INTELLIGENT SYSTEM OF VENTILATOR AND OPERATING METHOD THEREOF

(71) Applicant: Nanjing ChenWei Medical Equipment Co., Ltd, Nanjing (CN)

(72) Inventor: Ningxiang Ji, Nanjing (CN)

(73) Assignee: NANJING CHENWEI MEDICAL EQUIPMENT CO., LTD, Nanjing (CN)

( * ) Notice: Subject to any disclaimer, the term of this patent is extended or adjusted under 35 U.S.C. 154(b) by 856 days.

(21) Appl. No.: 16/978,832

(22) PCT Filed: Apr. 29, 2020

(86) PCT No.: PCT/CN2020/087851  
§ 371 (c)(1),  
(2) Date: Sep. 8, 2020

(87) PCT Pub. No.: WO2020/244347  
PCT Pub. Date: Dec. 10, 2020

(65) Prior Publication Data  
US 2021/0187220 A1    Jun. 24, 2021

(30) Foreign Application Priority Data  
Jun. 3, 2019    (CN) .......................... 201910478013.2

(51) Int. Cl.  
*A61M 16/00*    (2006.01)  
*G16H 20/40*    (2018.01)

(52) U.S. Cl.  
CPC ...... *A61M 16/0051* (2013.01); *A61M 16/024* (2017.08); *G16H 20/40* (2018.01); *A61M 2205/52* (2013.01)

(58) Field of Classification Search  
CPC ............ A61M 16/0051; A61M 16/024; A61M 2205/52; G16H 20/40  
See application file for complete search history.

(56) References Cited

U.S. PATENT DOCUMENTS

| 5,881,723 A | * | 3/1999 | Wallace | .............. A61M 16/024 |
| | | | | 128/204.23 |
| 2003/0062045 A1 | * | 4/2003 | Woodring | ......... A61M 16/0051 |
| | | | | 128/204.21 |

(Continued)

FOREIGN PATENT DOCUMENTS

| CN | 103781507 A | 5/2014 |
| CN | 104958074 A | 10/2015 |

(Continued)

*Primary Examiner* — Valerie L Woodward  
(74) *Attorney, Agent, or Firm* — Tutunjian & Bitetto, P.C.

(57) ABSTRACT

An intelligent ventilator system and operating method thereof are provided. The system includes a ventilator and an input system. The ventilator includes an alarm system, a monitoring system, a communication unit, and a ventilator control system, where the ventilator is configured to apply respiratory treatment to a patient. The input system is configured to input the patient's parameters and treatment requirements to realize recordings of original data of a designed treatment plan. The ventilator control system calculates target data needed by the patient and design the treatment plan, and to control the ventilator. The communication unit is configured for data communication between the input system and the ventilator control system to realize transfer of data from the input system to the ventilator control system. The monitoring system is configured for real-time monitoring of patients, and the alarm system is configured to alarm in time according to the patient's urgency.

4 Claims, 1 Drawing Sheet

(56) References Cited

U.S. PATENT DOCUMENTS

| | | |
|---|---|---|
| 2008/0011294 A1 | 1/2008 | Heesch et al. |
| 2008/0053441 A1* | 3/2008 | Gottlib .................. A61M 16/12 128/204.23 |
| 2010/0229867 A1* | 9/2010 | Bertinetti .......... A61M 16/0051 345/184 |
| 2011/0015944 A1* | 1/2011 | Gegner .................. A61B 5/145 705/2 |

FOREIGN PATENT DOCUMENTS

| | | |
|---|---|---|
| CN | 108568018 A | 9/2018 |
| CN | 109107007 A | 1/2019 |
| CN | 110368561 A | 10/2019 |

\* cited by examiner

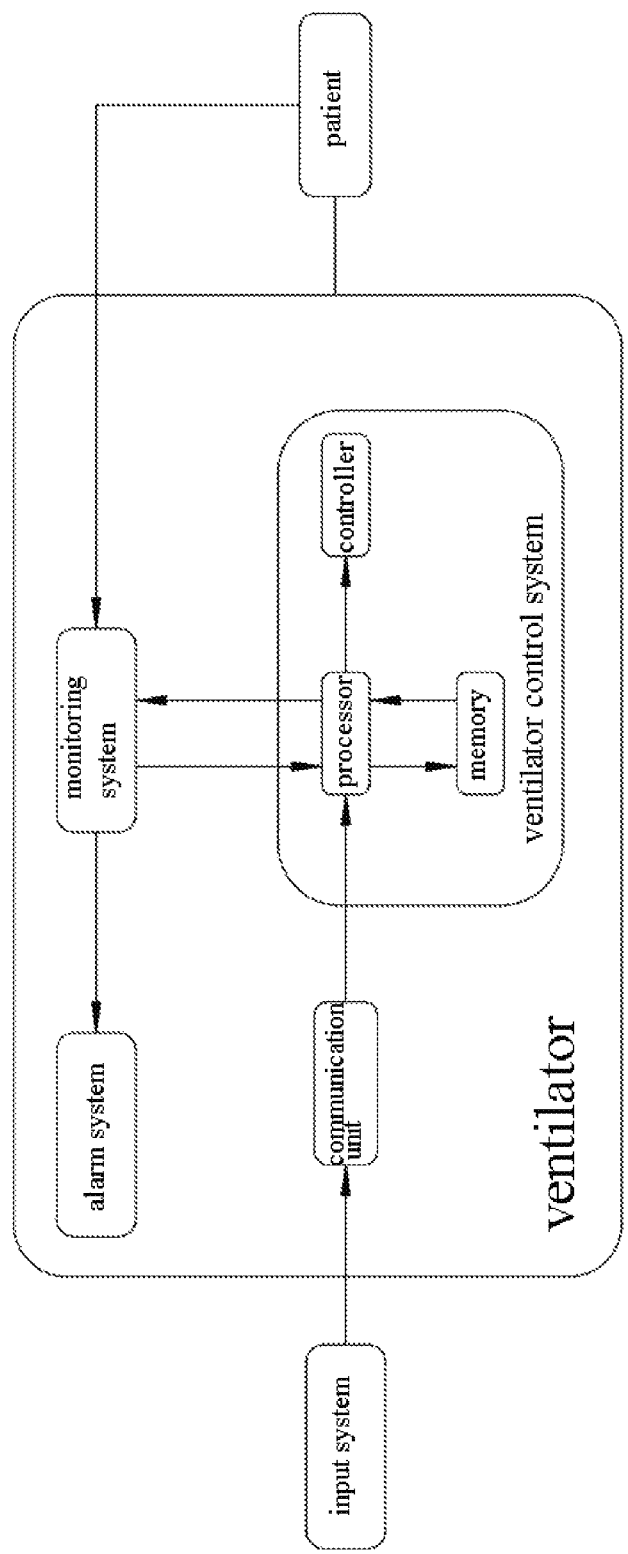

INTELLIGENT SYSTEM OF VENTILATOR AND OPERATING METHOD THEREOF

TECHNICAL FIELD

The present disclosure relates to the field of intelligent operation of ventilator, in particular to an intelligent system of ventilator and working method thereof.

BACKGROUND

In modern clinical medicine, as an effective method that can artificially replace autonomous ventilation, ventilator has been widely used in respiratory failure caused by various reasons, anesthesia breathing management during major operations, respiratory support treatment, and emergency resuscitation. Therefore, the ventilator occupies a very important position in the field of modern medicine. The ventilator is a vital medical device that can prevent and treat respiratory failure, thereby reducing complications, and saving and prolonging the lives of patients.

Technical Problem

Currently, various operating modes and methods of the therapeutic ventilators on the market are all manually judged and adjusted by medical staff according to the treatment goals and monitoring results. Such manually-operated ventilator requires a high technical level of medical staff, a constant change in operating modes and a constant adjustment in various parameters, to achieve the established treatment goals; therefore, an intelligent system of ventilator and operating method thereof is urgently needed to be developed on the market to help people solve those existing problems.

Technical Solution

The purpose of the present disclosure is to provide an intelligent system of ventilator and an operating method thereof. Through the close combination of a ventilator control system and a monitoring system, combined with clinical needs, the intelligence of the ventilator can be realized.

In order to achieve the above objectives, the present disclosure provides the following technical solutions: an intelligent system of ventilator and an operating method thereof, the intelligent system of ventilator includes a ventilator and an input system, wherein the ventilator comprises an alarm system, a monitoring system, a communication unit, and a ventilator control system;
wherein: the ventilator is used to apply respiratory treatment to a patient;
the input system is used to input the patient's parameters and treatment requirements to realize recordings of an original data of a designed treatment plan;
the ventilator control system is used to calculate a target data needed by the patient and design the treatment plan, and control the ventilator to realize an automatic operation of the ventilator;
the communication unit is used for data communication between the input system and the ventilator control system to realize transfer of data from the input system to the ventilator control system;
the monitoring system is used for real-time monitoring of patients;
the alarm system is used to alarm in time according to the patient's urgency and automatically enter an operating state of safety measures.

Preferably, the ventilator control system comprises a processor, a controller and a memory;
wherein: the processor is used to receive transmission data of the communication unit, process an abnormal situation monitored by the monitoring system, store and call data with the memory, and send the treatment plan to the controller to realize safe automatic operation of the ventilator;
the controller is used to receive the treatment plan of the processor and realize the control of an air-oxygen mixer and a humidifier of the ventilator;
the memory is used to store the target data calculated by the processor and the designed treatment plan of the patient.

An operating method of an intelligent system of ventilator, which includes the following steps:
step 1: an operator inputs the patient's parameters and treatment requirements to the ventilator through an input system, and a communication unit serves as an intermediate communication component to send data to a processor;
step 2: the processor calculates a target data needed by the patient and designs a treatment plan according to the patient's parameters and treatment requirements, and stores the data and plan into the memory, then through controlling of a controller, the ventilator operates automatically according to the designed plan;
step 3: when the ventilator is operating according to a set mode parameters and time, a monitoring system continuously monitors the patient in real time and sends monitoring data back to the processor;
step 4: the processor compares the returned monitoring data with the preset target data in the memory, if a preset effect is not reached, the ventilator will automatically prompt;
step 5: when the patient has an emergency and reaches a set warning value, the ventilator will give an alarm through the alarm system and automatically enter an operating state of safety measures.

Preferably, when the ventilator is operating according to the set mode parameters and time, a new treatment plan can be set according to an actual operating condition and stored in the memory.

Beneficial Effect

Compared with the prior art, the beneficial effects of the present disclosure are:
1. In this disclosure, the patient's parameters and treatment requirements, such as the patient's weight and age, are input through the input system, and the data transmission is completed through the communication unit, without the need to manually judge and adjust the operating mode of the ventilator according to the treatment target;
2. In this disclosure, the processor calculates the target data required by the patient and designs the treatment plan according to the patient's parameters and treatment requirements. Through the control of the controller, the ventilator automatically operates according to the designed plan, thereby realizing the automatic operation of the ventilator without manually setting the operating mode;

In this disclosure, when the ventilator is operating according to the set mode parameters and time, the patient is continuously monitored by the monitoring system in real time, and then the monitored data is compared with the preset target data. If the preset effect is not achieved, the ventilator will automatically prompt, if the patient has an emergency, the ventilator will also promptly alarm according to the emergency. Compared with the traditional way that the medical staff constantly change operating modes and adjust various parameters according to operating conditions to achieve the established treatment goals, the present disclosure has lower requirements on the technical level of medical staff, and therefore the work pressure of medical staff can be relieved.

BRIEF DESCRIPTION OF THE DRAWINGS

FIG. 1 is a schematic diagram of the operation of an intelligent system of ventilator and operating method thereof according to the present disclosure.

DETAILED DESCRIPTION

The technical solutions in the embodiments of the present disclosure will be clearly and completely described below in conjunction with the accompanying drawings in the embodiments of the present disclosure. Apparently, the described embodiments are only a part of the embodiments of the present disclosure, rather than all of them.

Referring to FIG. 1, an embodiment provided by the present disclosure: an intelligent system of ventilator and operating method thereof, including a ventilator and an input system, the ventilator including an alarm system, a monitoring system, a communication unit, and a ventilator control system;

Wherein, the ventilator is used to provide respiratory treatment to the patient. The ventilator mainly includes a gas source, an air-oxygen mixer, a humidifier and an external pipeline. The controller controls the operation of the air-oxygen mixer and the degree of steam supplied by the humidifier, which is transmitted to the breathing mask through the external pipeline to perform respiratory treatment on the patient;

The input system is used to input the patient's parameters and treatment requirements, and realize the record of the original data of the designed treatment plan. The parameters include the patient's weight, age, and the reason for respiratory treatment, an appropriate plan is thus calculated according to the patient's condition and which does not exceed the treatment range that the patient's body can withstand. The input system can be a computer, and the form of the input system is not limited, and it can be adjusted according to the actual case;

The ventilator control system is used to calculate the target data needed by the patient and design the treatment plan, wherein, the ventilator control system is connected with an external network. The ventilator control system can adjust the designed plan according to many respiratory treatment cases, and control the ventilator to realize the automatic operation of the ventilator. Compared with the traditional way that the medical staff constantly change the operating mode and adjust various parameters according to the operating conditions to achieve the established treatment goals, the present disclosure can alleviate the work pressure of the medical staff;

The communication unit is used for the data communication between the input system and the ventilator control system to realize the transfer of data from the input system to the ventilator control system. The communication unit may be a Bluetooth module, a wireless communication module, a 4G module, or a combination of two of them, or a combination of three, which can be adjusted according to the actual situation;

The monitoring system is used for real-time monitoring of the patient, returning the monitoring data to the processor. The processor compares the returned monitoring data with the preset target data in the memory. If a preset effect is not achieved, the ventilator will automatically prompt;

The alarm system is used to alarm in time according to the urgency of the patient and automatically enters an operating state of safety measures. There is no specific operating state for safety measures, but a preset respiratory treatment program is started, which is set up while the patient's parameters and treatment requirements are input into the input system. While there is no perfect treatment, this will minimize the harm to the patient. And wait for the medical staff to proceed with the next step, which will manually adjust the operating mode to adjust the respiratory treatment plan.

Further, the ventilator control system includes a processor, a controller and a memory;

wherein, the processor is used to receive the transmission data of the communication unit, handle the abnormal situation monitored by the monitoring system, store and call the data with the memory, and send the treatment plan to the controller to realize the safe automatic operation of the ventilator. In order to ensure the operating speed of the processor, the model of the processor is not regulated, but is adjusted in real time according to the actual scientific and technological development to lay a solid foundation for the patient's respiratory treatment;

The controller is used to receive the treatment plan of the processor, thereby realizing the control of the air-oxygen mixer and humidifier of the ventilator, and controlling the oxygen supply to adjust the oxygen concentration and the oxygen humidity according to the treatment plan;

The memory is used to store the target data of the patient calculated by the processor and to design the treatment plan. The memory includes main storage and backup storage to avoid medical accidents caused by abnormal data loss.

An operating method of an intelligent system of ventilator, which includes the following steps:

At step 1: the operator inputs the patient's parameters and treatment requirements to the ventilator through the input system, and at the same time presets the mode of the operation state of safety measure to ensure that the operation state of safety measure will causes minimal damage to the patient, and the communication unit serves as an intermediate communication component to send data to the processor;

At step 2: the processor calculates the target data needed by the patient and designs the treatment plan according to the patient's parameters and treatment requirements, and stores the data and plan into the memory for easy recall and to ensure that the data is not lost. Through the control of the controller, the ventilator operates automatically according to the designed plan;

At step 3: when the ventilator is operating according to the set mode parameters and time, the monitoring system continuously monitors the patient in real time and sends the monitoring data back to the processor;

At step 4: the processor compares the returned monitoring data with the preset target data in the memory. If a preset effect is not achieved, the ventilator will automatically prompt;

At step 5: when the patient has an emergency and reaches a set warning value, the ventilator will give an alarm through the alarm system and automatically enter an operating state of safety measures, and to inform the medical staff whether to change the design plan in the next step. At this time, the medical staff can choose to operate the ventilator normally according to the original situation or continue operation after changing the plan (which is manually modified) according to the situation.

Furthermore, when the ventilator is operating according to the set mode parameters and time, a new treatment plan can be set according to the actual operating conditions and stored in the memory. In the correction of human-computer interaction, while achieving the target effect, the working time of medical staff is greatly reduced and work efficiency is thus improved.

For those skilled in the art, it is obvious that the present disclosure is not limited to the details of the above exemplary embodiments, and the present disclosure can be implemented in other specific forms without departing from the spirit or basic characteristics of the present disclosure. Therefore, regardless of the point of view, the embodiments should be regarded as exemplary and non-limiting. The scope of the present disclosure is defined by the appended claims rather than the above description, therefore, it is intended that all changes falling within the meaning and scope of equivalent elements of the claims are included in the present disclosure. Any reference signs in the claims should not be regarded as limiting the involved claims.

What is claimed is:

1. An intelligent system of a ventilator, comprising the ventilator and an input system, wherein the ventilator comprises an alarm system, a monitoring system, a communication unit, and a ventilator control system;
   wherein:
   the ventilator is used to apply respiratory treatment to a patient;
   the input system is used to input original data comprising the patient's parameters and treatment requirements to realize recordings of the original data of a designed treatment plan;
   the ventilator control system is used to calculate a target data needed by the patient and design the treatment plan, and control the ventilator to realize an automatic operation of the ventilator;
   the communication unit is used for data communication between the input system and the ventilator control system to realize transfer of the original data from the input system to the ventilator control system;
   the monitoring system is used for real-time monitoring of patients;
   the alarm system is used to alarm in time according to the patient's urgency and the ventilator automatically enter an operating state of safety measures, wherein the operating state of safety measures is a predetermined respiratory treatment program and is set up while the patient's parameters and treatment requirements are input into the input system.

2. The intelligent system of claim 1, wherein the ventilator control system comprises a processor, a controller and a memory;
   wherein:
   the processor is used to receive the original data transmitted from the communication unit, process an abnormal situation monitored by the monitoring system, perform data storage and call with the memory, and send the treatment plan to the controller to realize safe automatic operation of the ventilator;
   the controller is used to receive the treatment plan of the processor and realize the control of an air-oxygen mixer and a humidifier of the ventilator;
   the memory is used to store the target data calculated by the processor and the designed treatment plan of the patient.

3. An operating method of an intelligent system of a ventilator, comprising the following steps:
   Step 1: an operator inputs original data comprising a patient's parameters and treatment requirements to the ventilator through an input system, and a communication unit serves as an intermediate communication component to send the original data to a processor;
   step 2: the processor calculates a target data needed by the patient and designs a treatment plan according to the patient's parameters and treatment requirements, and stores the target data and the treatment plan into a memory, and through controlling of a controller, the ventilator operates automatically according to the treatment plan;
   step 3: when the ventilator is operating according to set mode parameters and time, a monitoring system continuously monitors the patient in real time and sends monitoring data back to the processor;
   step 4: the processor compares the returned monitoring data with the target data in the memory, if a preset effect is not reached, the ventilator automatically prompts;
   step 5: when the patient has an emergency and reaches a predetermined warning value, the ventilator gives an alarm through the alarm system and automatically enter an operating state of safety measures, wherein the operating state of safety measures is a predetermined respiratory treatment program and is set up while the patient's parameters and treatment requirements are input into the input system.

4. The operating method of claim 3, wherein, when the ventilator is operating according to the set mode parameters and time, a new treatment plan is adapted to be set according to an actual operating condition and stored in the memory.

* * * * *